US009226655B2

(12) United States Patent
Iwase et al.

(10) Patent No.: US 9,226,655 B2
(45) Date of Patent: Jan. 5, 2016

(54) IMAGE PROCESSING APPARATUS AND IMAGE PROCESSING METHOD

(71) Applicant: CANON KABUSHIKI KAISHA, Tokyo (JP)

(72) Inventors: Yoshihiko Iwase, Kyoto (JP); Tomoyuki Makihira, Tokyo (JP); Kazuhide Miyata, Yokohama (JP); Makoto Sato, Tokyo (JP); Kazuro Yamada, Kawasaki (JP); Ritsuya Tomita, Kawasaki (JP); Daisuke Kibe, Chigasaki (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/851,882

(22) Filed: Mar. 27, 2013

(65) Prior Publication Data

US 2013/0258285 A1 Oct. 3, 2013

(30) Foreign Application Priority Data

Mar. 30, 2012 (JP) ................................ 2012-082375

(51) Int. Cl.

| | |
|---|---|
| ***A61B 3/14*** | (2006.01) |
| ***A61B 3/10*** | (2006.01) |
| ***G06K 9/00*** | (2006.01) |
| ***G06T 7/00*** | (2006.01) |

(52) U.S. Cl.
CPC ............... *A61B 3/102* (2013.01); *G06T 7/0012* (2013.01); *G06T 2207/10101* (2013.01); *G06T 2207/30041* (2013.01)

(58) Field of Classification Search
CPC ............... A61B 3/00; A61B 3/10; A61B 3/14
USPC .................. 351/206, 205, 221, 210, 200, 246
See application file for complete search history.

(56) References Cited

U.S. PATENT DOCUMENTS

| | | | | |
|---|---|---|---|---|
| 5,321,501 | A | 6/1994 | Swanson et al. | |
| 2007/0070295 | A1 | 3/2007 | Tsukada et al. | |
| 2008/0084538 | A1 * | 4/2008 | Maeda et al. | 351/206 |
| 2008/0100612 | A1 | 5/2008 | Dastmalchi et al. | |
| 2008/0151187 | A1 * | 6/2008 | Tsukada et al. | 351/206 |
| 2010/0189817 | A1 * | 7/2010 | Krueger et al. | 424/718 |

(Continued)

FOREIGN PATENT DOCUMENTS

| | | | |
|---|---|---|---|
| JP | 2007-117714 | A | 5/2007 |
| WO | WO 2011013314 | A1 * | 2/2011 |
| WO | 2011/122007 | A2 | 10/2011 |

OTHER PUBLICATIONS

U.S. Appl. No. 13/851,846, filed Mar. 27, 2013, Tomoyuki Makihira.

*Primary Examiner* — Dawayne A Pinkney
(74) *Attorney, Agent, or Firm* — Canon USA, Inc. I.P. Division

(57) ABSTRACT

An image processing apparatus includes an obtaining unit configured to obtain a tomographic image including an optic disc portion and a macula portion of a fundus of a subject's eye, an analysis unit configured to analyze the optic disc portion and the macula portion of the fundus in the tomographic image, and a display control unit configured to display side-by-side, on a display unit, a display pattern indicating a result of analyzing the optic disc portion, and a display pattern indicating a result of analyzing the macula portion.

3 Claims, 11 Drawing Sheets

(56) References Cited

U.S. PATENT DOCUMENTS

2010/0238403 A1 9/2010 Kobayashi et al.
2012/0121158 A1* 5/2012 Sekine et al. ................ 382/131
2012/0194783 A1* 8/2012 Wei et al. ..................... 351/206
2012/0281184 A1* 11/2012 Torii et al. .................... 351/206

* cited by examiner

IMAGE PROCESSING APPARATUS AND IMAGE PROCESSING METHOD

BACKGROUND OF THE INVENTION

1. Field of the Invention

The present invention relates to an image processing apparatus for processing a tomographic image of the fundus of a subject's eye, and a method for processing the tomographic image.

2. Description of the Related Art

An ocular tomographic imaging apparatus, such as an optical coherence tomograph (OCT), is capable of three-dimensionally observing a state inside the retina layer. In recent years, this tomographic imaging apparatus has attracted attention for the usability for performing disease diagnoses with higher accuracy.

A time domain OCT (TD-OCT) combining a wide-band light source with a Michelson interferometer is a form of the OCT. The TD-OCT scans a delay of a reference arm to measure interference light of backward scattering light of a signal arm and light from the reference arm, thus obtaining information about the depth resolution. However, high-speed image acquisition is difficult to achieve by using such a TD-OCT. Accordingly, as a method for obtaining an image at higher speed, a spectral domain OCT (SD-OCT) is known to obtain an interferogram by using a wide-band light source and a spectroscope. Further, a swept source OCT (SS-OCT) is known to employ a technique for measuring spectrum interference by using a high-speed wavelength sweep light source and a single channel photodetector (as discussed in U.S. Pat. No. 5,321,501). The spectroscope used by the SD-OCT splits and diffracts interference light by using a diffraction grating in space. Therefore, crosstalk interference light may easily occur between adjacent pixels of a line sensor. Interference light from a reflection surface located at a depth position $Z=Z0$ vibrates at a frequency $Z0/n$ with respect to the number of waves k. Therefore, with increasing depth position $Z0$ (specifically, with increasing distance from the coherence gate position), an oscillating frequency of the interference light increases, resulting in increased effects of crosstalk of the interference light between adjacent pixels of the line sensor. This means that, with the SD-OCT, performing tomographic imaging at a deeper position causes remarkable degradation in sensitivity. On the other hand, the SS-OCT which does not use a spectroscope is more advantageous in tomographic imaging at a deep position than the SD-OCT.

Further, the spectroscope of the SD-OCT causes a loss of interference light due to the diffraction grating. With the SS-OCT on the other hand, the sensitivity can be easily improved, for example, by performing differential detection of interference light without using a spectroscope. Therefore, the processing speed of the SS-OCT can be improved with an equivalent sensitivity to that of the SD-OCT. The high processing speed enables obtaining a tomographic image having a wide viewing angle.

SUMMARY OF THE INVENTION

An embodiment of the present invention is directed to an image processing apparatus that efficiently presents a result of analyzing a tomographic image having a wide viewing angle and a large depth in the depth direction obtained by the SS-OCT.

The present invention is not limited thereto, and may also be directed to providing effects which are led by configurations described in exemplary embodiments described below and cannot be obtained by conventional techniques.

According to an aspect of the present invention, an image processing apparatus includes an obtaining unit configured to obtain a tomographic image including an optic disc portion and a macula portion of a fundus of a subject's eye, an analysis unit configured to analyze the optic disc portion and the macula portion of the fundus in the tomographic image, and a display control unit configured to display side-by-side, on a display unit, a display pattern indicating a result of analyzing the optic disc portion, and a display pattern indicating a result of analyzing the macula portion.

According to an exemplary embodiment of the present invention, it is possible to display, on a display unit, a display pattern indicating a result of analyzing the optic disc and the macula of the fundus in a tomographic image of the fundus, and to display the tomographic image. This enables efficiently presenting a result of analyzing a tomographic image having a wide viewing angle and a large depth in the depth direction obtained by the SS-OCT.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

The first exemplary embodiment of the present invention will be described in detail below with reference to the accompanying drawings.

[Overall Configuration of the Image Processing Apparatus]

Figure 1:
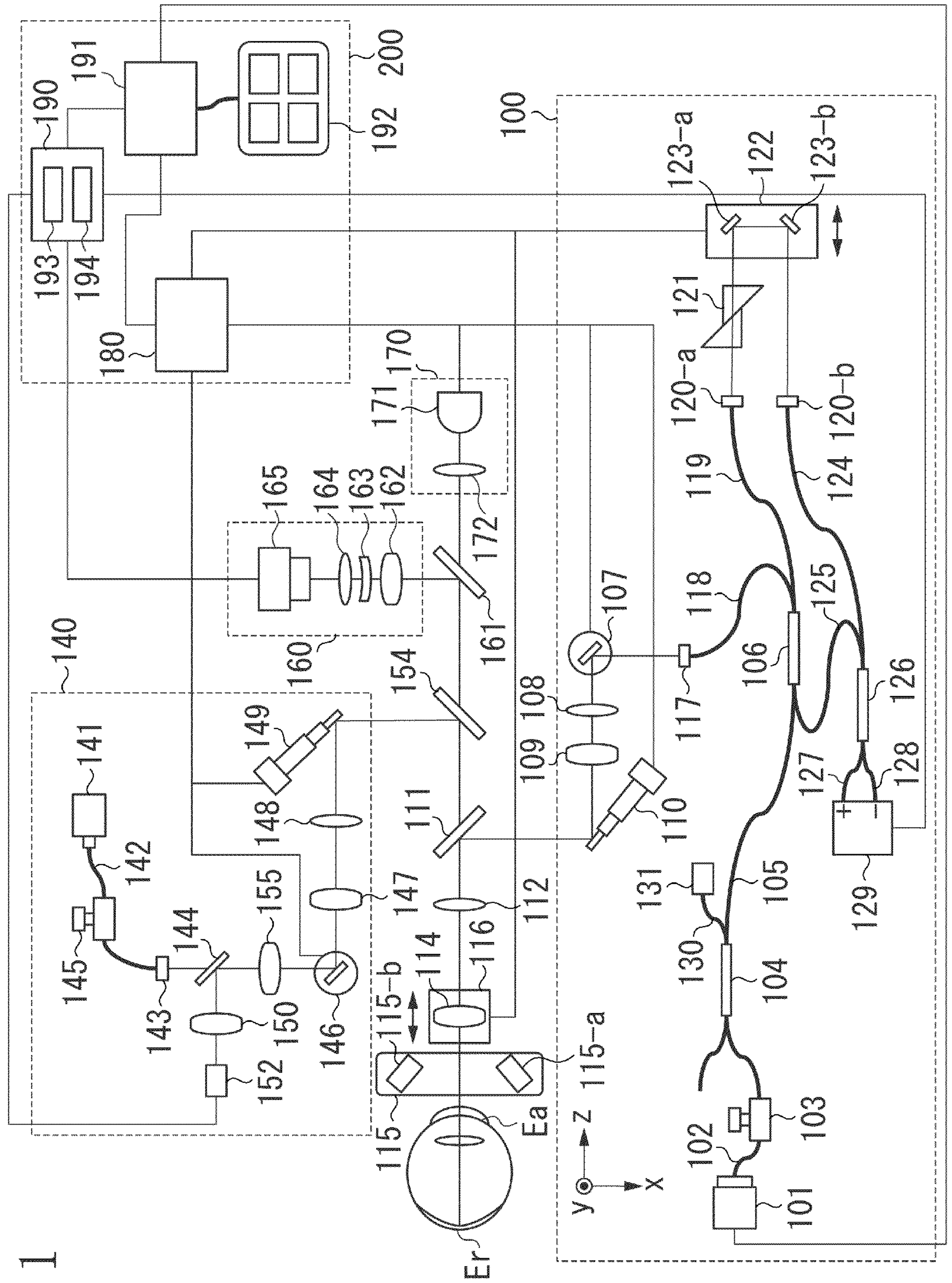
FIG. 1 is a schematic view illustrating an overall configuration of an image processing apparatus according to a first exemplary embodiment of the present invention.

FIG. 1 is a schematic view illustrating an overall configuration of an image processing apparatus according to the present exemplary embodiment.

The image processing apparatus includes a swept source OCT (SS-OCT) 100, a scanning laser ophthalmoscope (SLO) 140, an anterior ocular segment imaging unit 160, an internal fixation lamp 170, and a control unit 200.

With the internal fixation lamp 170 turned ON and with the subject's eye fixed, alignment of the image processing apparatus is performed by using an image of the anterior ocular segment of the subject's eye observed by the anterior ocular segment imaging unit 160. After completion of alignment, the OCT 100 and SLO 140 capture an image of the fundus.

<Configuration of the OCT 100>

The configuration of the OCT 100 will be described below.

A light source 101 (variable wavelength light source) emits light having, for example, a center wavelength of 1040 nm and a bandwidth of 100 nm. The light emitted from the light source 101 advances through a fiber 102 and a polarization controller 103 and reaches a fiber coupler 104. The fiber coupler 104 branches the light to a fiber 130 for light quantity measurement and a fiber 105 for OCT measurement. Then, the light emitted from the light source 101 advances through a fiber 130 and reaches a power meter (PM) 131 which measures the power of the light. The light from the light source 101 also advances through the fiber 105 and reaches a second fiber coupler 106. The fiber coupler 106 branches the light into a measuring beam (also referred to as an OCT measuring beam) and a reference beam. The polarization controller 103 adjusts the polarization state of the light emitted from the light source 101 to linearly polarized light. The branching ratio of the fiber coupler 104 is 99:1, and the branching ratio of the fiber coupler 106 is 90:10 (reference beam:measuring beam).

The measuring beam branched by the fiber coupler 106 advances through a fiber 118 and reaches a collimator 117. The collimator 117 emits the measuring beam as parallel light. The emitted measuring beam passes through an X scanner 107 (including a galvanometer mirror for horizontally scanning a fundus Er with the measuring beam), lenses 108 and 109, and a Y scanner 110 (including a galvanometer mirror for vertically scanning the fundus Er with the measuring beam), and then reaches a dichroic mirror 111. The X scanner 107 and the Y scanner 110 are controlled by a drive control unit 180 to scan regions in a desired range on the fundus Er by using the measuring beam. The dichroic mirror 111 has the characteristics of reflecting light having a wavelength of 950 nm to 1100 nm and transmitting light other than the light in that wavelength range.

The measuring beam reflected by the dichroic mirror 111 passes through the lens 112 and then reaches a focus lens 114 mounted on a stage 116. The focus lens 114 focuses the measuring beam onto the retina layer of the fundus Er of the subject's eye via an anterior ocular segment Ea. The measuring beam radiated onto the fundus Er reflects off and scatters on each retina layer, advances through the above-described optical path in the opposite direction, and then returns to the fiber coupler 106. The measuring beam from the fundus Er departs the fiber coupler 106, advances through a fiber 125 and then reaches the fiber coupler 126.

On the other hand, the reference beam branched by the fiber coupler 106 advances through a fiber 119 and reaches a collimator 120-*a*. The collimator 120-*a* emits the reference beam as parallel light. The emitted reference beam passes through a dispersion compensation glass 121, reflects off mirrors 123-*a* and 123-*b* on a coherence gate stage 122, advances through a collimator 120-*b* and a fiber 124, and then reaches the fiber coupler 126. The coherence gate stage 122 corresponds to a difference in optic axis length of the subject's eye, and therefore is controlled by the drive control unit 180.

The measuring beam and the reference beam having reached the fiber coupler 126 are combined into interference light which then advances through fibers 127 and 128 and reaches a balanced receiver (photodetector) 129. The balanced receiver 129 converts the interference light into an electrical signal. A signal processing unit 190 analyzes the electrical signal.

<Configuration of the SLO 140>

The configuration of the SLO 140 will be described below.

A light source 141 (semiconductor laser) emits a measuring beam having, for example, a center wavelength of 780 nm in the present exemplary embodiment. The measuring beam (also referred to as an SLO measuring beam) emitted from the light source 141 advances through a fiber 142 and reaches a polarization controller 145. The polarization controller 145 adjusts the measuring beam into linearly polarized light. A collimator 143 emits the polarized light as a parallel light. The emitted measuring beam passes through a hole on a perforated mirror 144, and passes through a lens 155, an X scanner 146 (including a galvanometer mirror for horizontally scanning the fundus Er with the measuring beam), lenses 147 and 148, and a Y scanner 149 (including a galvanometer mirror for vertically scanning the fundus Er with the measuring beam), and then reaches a dichroic mirror 154. The X scanner 146 and the Y scanner 149 under the control of the drive control unit 180 enable scanning a desired range on the fundus Er by using the measuring beam. The dichroic mirror 154 has the characteristics of reflecting light having a wavelength of 760 nm to 800 nm and transmitting light other than the light in that wavelength range.

The measuring beam of the linearly polarized light reflected by the dichroic mirror 154 transmits the dichroic mirror 111, advances through the same optical path as the OCT measuring beam of the OCT 100, and then reaches the fundus Er.

The SLO measuring beam radiated onto the fundus Er reflects off and scatters on the fundus Er, advances through the above-described optical path, and then reaches the perforated mirror 144. The light reflected by the perforated mirror 144 advances through a lens 150 and then reaches an avalanche photodiode (APD) 152. The APD 152 converts the light into an electrical signal, and the signal processing unit 190 receives the relevant signal.

The position of the perforated mirror 144 is conjugate to the pupil position of the subject's eye. The measuring beam radiated on the fundus Er reflects off and scatters on the fundus Er, partly passes through the pupil periphery, and reflects off the perforated mirror 144.

<Anterior Ocular Segment Imaging Unit 160>

The anterior ocular segment imaging unit 160 will be described below.

The anterior ocular segment imaging unit 160 irradiates the anterior ocular segment Ea with light from an illumination light source 115. The illumination light source 115 includes light emitting diodes (LEDs) 115-*a* and 115-*b* for emitting illumination light having a wavelength of 850 nm. The light reflected by the anterior ocular segment Ea passes through the lenses 114 and 112 and the dichroic mirrors 111 and 154 and then reaches the dichroic mirror 161. The dichroic mirror 161 has the characteristics of reflecting light having a wavelength of 820 nm to 900 nm and transmitting light other than the light in that wavelength range. The light reflected by the dichroic mirror 161 passes through lenses 162, 163, and 164 and then is received by an anterior ocular segment camera 165. The anterior ocular segment camera 165 converts the received light into an electrical signal, and the signal processing unit 190 receives the relevant signal.

<Internal Fixation Light 170>

The internal fixation lamp 170 will be described below.

The internal fixation lamp 170 includes a display 171 and a lens 172. The display 171 includes a plurality of LEDs arranged in matrix form. The LED lighting position is controlled by the drive control unit 180, and changed according to a target portion. The light from the display 171 advances through the lens 172 and then reaches the subject's eye. The display 171 emits light having a wavelength of 520 nm. A desired pattern is displayed by the drive control unit 180.

<Control Unit 200>

The control unit 200 will be described below.

The control unit 200 includes the drive control unit 180, the signal processing unit 190, the control unit 191, and the display unit 192.

The drive control unit 180 controls the above-described units.

Figure 6A:
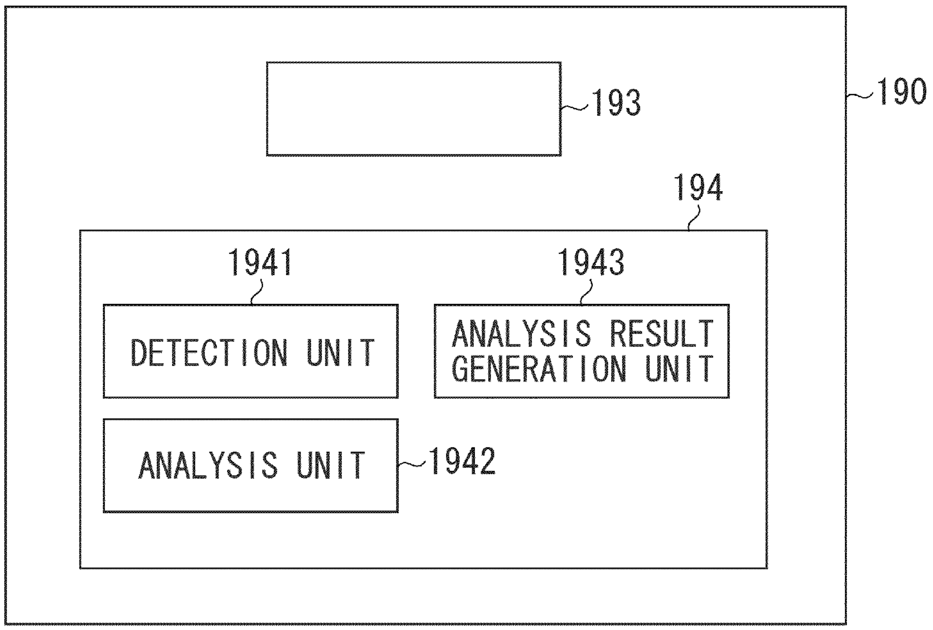
FIGS. 6A and 6B illustrate a configuration of a signal processing unit according to first and second exemplary embodiments of the present invention, respectively.

The signal processing unit 190 includes an image generation unit 193 and an image analysis unit 194. The configuration of the signal processing unit 190 is illustrated in FIG. 6A. The signal processing unit 190 generates an image, analyzes the generated image, and generates visualized information of a result of the analysis (display pattern indicating the analysis result) based on signals output from the balanced receiver 129, the APD 152, and the anterior ocular segment camera 165. Processing for image generation and image analysis will be described in detail below.

The control unit 191 controls the entire apparatus, and displays, on a display screen of the display unit 192, the image generated by the signal processing unit 190. A display control unit for displaying an image on the display screen of the display unit 192 may be separately provided.

Under the control of the control unit 191, the display unit 192 displays various information described below.

[Image Processing]

Processing for image generation by the image generation unit 193 will be described below.

<Tomographic Image Generation and Fundus Image Generation>

The image generation unit 193 applies general reconstruction processing to each interference signal output from the balanced receiver 129 to generate a tomographic image.

The image generation unit 193 eliminates fixed pattern noise from the interference signal. To eliminate fixed pattern noise, the image generation unit 193 averages a plurality of detected A-scan signals to extract fixed pattern noise and then subtracts the extracted noise from the input interference signal.

Then, the image generation unit 193 performs required window function processing to optimize the depth resolution and the dynamic range which is in a trade-off relation when Fourier transform is applied to a limited section. Then, the image generation unit 193 performs fast Fourier transform (FFT) processing to generate a tomographic signal.

Figure 2:
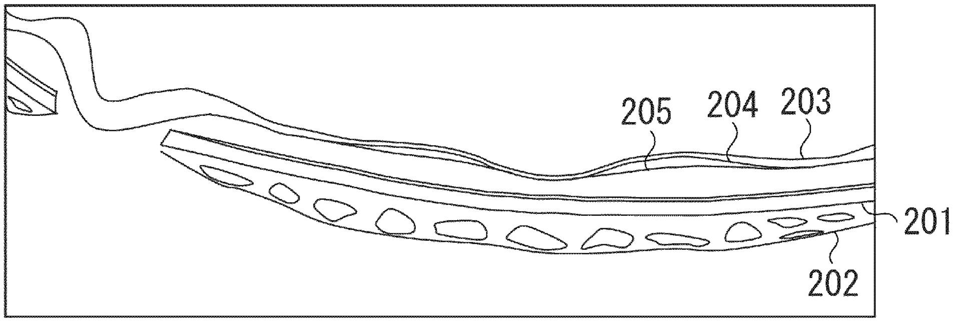
FIG. 2 illustrates an example tomographic image obtained by capturing an image of a subject's eye by using an optical coherence tomographic imaging apparatus according to the first exemplary embodiment.

FIG. 2 illustrates an example tomographic image captured by the OCT 100 and generated by the image generation unit 193. FIG. 2 illustrates the boundary 201 (Bruch membrane) between the retinal pigment epithelium and the choroid membrane, the boundary 202 between the choroid membrane and the sclerotic membrane, the boundary 203 between the internal limiting membrane (ILM) and the retinal nerve fiber layer (RNFL), the boundary 204 between the retinal nerve fiber layer (RNFL) and the ganglion cell layer (GCL), and the boundary 205 between the ganglion cell layer (GCL) and the inner plexiform layer (IPL). In the present exemplary embodiment, the OCT 100 is an SS-OCT including a 1040-nm-long wavelength light source, providing deeper measurement light to the subject's eye and high-speed signal acquisition. Thus, an image of a wider range can be captured within the same time duration. Therefore, up to the boundary 202 between the choroid membrane and the sclerotic membrane in the depth direction as illustrated in FIG. 2, the macula and optic disc can be drawn in the same tomogram.

[Processing and Operations]

Processing performed by the image processing apparatus will be described below.

Figure 3:
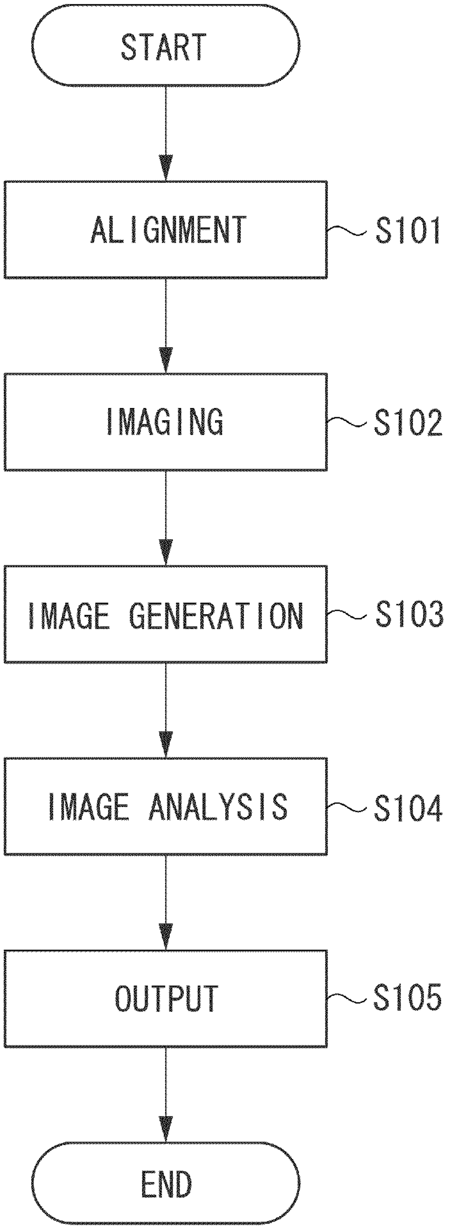
FIG. 3 is a flowchart illustrating processing performed by the image processing apparatus according to the first exemplary embodiment.

FIG. 3 is a flowchart illustrating processing performed by the image processing apparatus.

<Adjustment>

In step S101, the image processing apparatus performs alignment of the image processing apparatus and the subject's eye in a state where the subject's eye is placed on the image processing apparatus. During the alignment, the image processing apparatus adjusts the working distance, focus, and coherence gate.

<Adjustment of the OCT Imaging Position>

Figure 4:
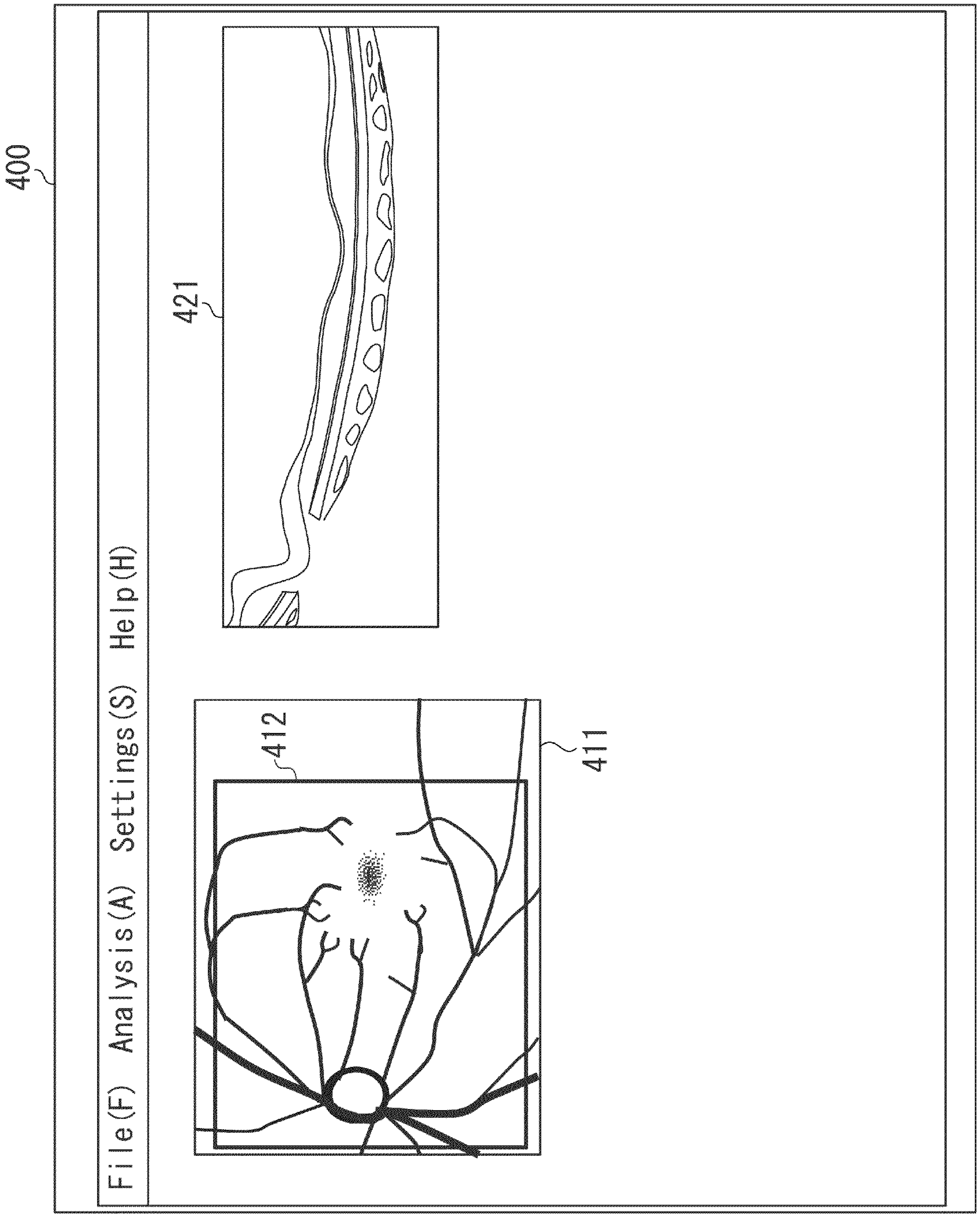
FIG. 4 illustrates an example imaging display screen according to the first exemplary embodiment.

FIG. 4 illustrates a window 400 displayed on the display unit 192 at the time of adjustment.

By using a pointing device (not illustrated) such as a mouse, an operator instructs the imaging mode with a cursor.

The instructed imaging mode is set based on the instruction, and a fundus image (luminance image) 411 captured by the SLO 140 and generated by the signal processing unit 190 is displayed. Then, according to the set imaging mode, an index indicating an imaging range 412 of the OCT 100 is superimposed onto the fundus image 411.

When the operator instructs with the cursor by using a pointing device (not illustrated) such as a mouse, an imaging range is set under the control of the drive control unit 180. Specifically, when the operator sets the size and adjusts the position of the imaging range 412 by using the cursor, the drive control unit 180 controls the driving angle of the scanners to set the imaging range 412. Referring to the example illustrated in FIG. 4, a three-dimensional image is obtained, and a tomographic image 421 in the vicinity of the center of the region is displayed.

<Image Capturing to Image Generation>

In step S102, based on an imaging instruction from the operator, the light sources 101 and 141 emit a measuring beam, the balanced receivers 129 and APD 152 receive returned light from the retina Er, and the signal processing unit 190 generates each image (step S103) as described above.

<Image Analysis>

The image analysis unit 194 includes a detection unit 1941, an analysis unit 1942, and an analysis result generation unit 1943.

The detection unit 1941 segments a tomographic image by using the above-described luminance image. The detection unit 1941 applies an median filter and a Sobel filter to a target tomographic image to generate a median image and a Sobel image, respectively. Then, the detection unit 1941 generates a profile for each A-scan based on the generated median image and Sobel image. Specifically, the detection unit 1941 generates a luminance profile based on the median image, and a gradient profile based on the Sobel image. Then, the detection unit 1941 detects peaks in the profile generated based on the Sobel image. Referring to the profile generated based on the median image corresponding to portions before and after the detected peaks and portions between the peaks, the detection unit 1941 extracts boundaries between retina layer regions (for example, the boundaries 201 to 205).

The analysis unit 1942 measures the thickness of each layer in the A-scan line direction by using the retina layer boundary detected by the detection unit 1941.

Further, the analysis result generation unit 1943 generates a two-dimensional layer thickness map and a layer thickness graph based on the thickness of each layer measured by the analysis unit 1942.

<Output>

Processing for outputting generated images and an analysis result in step S105 will be described below.

When the signal processing unit 190 completes generation and analysis of each image, the control unit 191 generates output information and outputs the information to the display unit 192.

[Display Screen]

Figure 5:
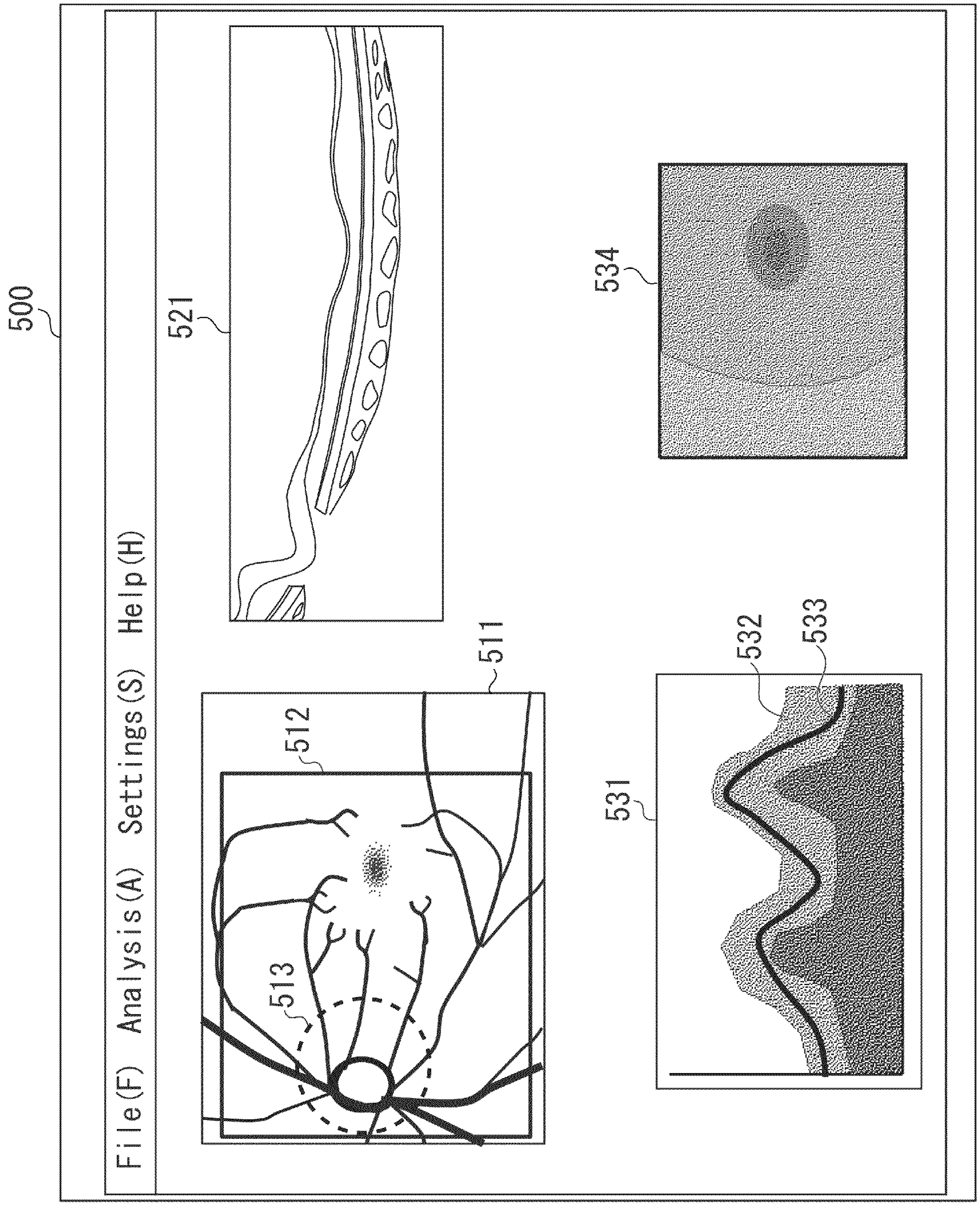
FIG. 5 illustrates an example display of an analysis result according to the first exemplary embodiment.

FIG. 5 illustrates example display of analysis results on the display unit 192 according to the present exemplary embodiment. FIG. 5 illustrates a fundus image 511, a tomographic image 521, analysis results 531 and 534, and analysis positions 512 and 513.

The analysis position 512 is the same as the imaging range 412, which indicates a range subjected to layer thickness map display. Referring to FIG. 5, the analysis result 534 is a layer thickness map in the range of the analysis position 512. The layer thickness map of the analysis result 534 displays, for example, the thickness of the RNFL and GCL between the boundaries 203 and 205, or the thickness of the choroid membrane between the boundaries 201 and 202.

The analysis position 513 indicates the position corresponding to the optic disc circle scan in the imaging range 412. The analysis result 531 is a thickness graph at the analysis position 513. Referring to the analysis result 531, a solid line 533 indicates a measured thickness graph (for example, the nerve fiber layer thickness), and a region 532 indicates example ranges of normal and abnormal layer thicknesses according to a statistics database.

As described above, the present exemplary embodiment enables efficiently presenting a result of measuring the retina layer in the optic disc periphery and a result of measuring the retina layer in the macula periphery in a tomographic image having a wide viewing angle and a large depth in the depth direction obtained by the SS-OCT. Thus, a loss of the RNFL at the optic disc, a loss of the GCL at the macula, and a reduction in thickness of the choroid membrane can be grasped at the same time. Therefore, in a glaucoma diagnosis, information for grasping changes in layer thickness at the optic disc and the macula can be efficiently presented.

In the first exemplary embodiment, a result of measuring the layer thickness in the optic disc periphery and a result of measuring the layer thickness in the macula periphery are presented in a tomographic image having a wide viewing angle obtained by the SS-OCT. In a second exemplary embodiment of the present invention, a result of analyzing the shape of the optic disc periphery and a result of analyzing the shape of the macula periphery are presented.

Figure 6B:
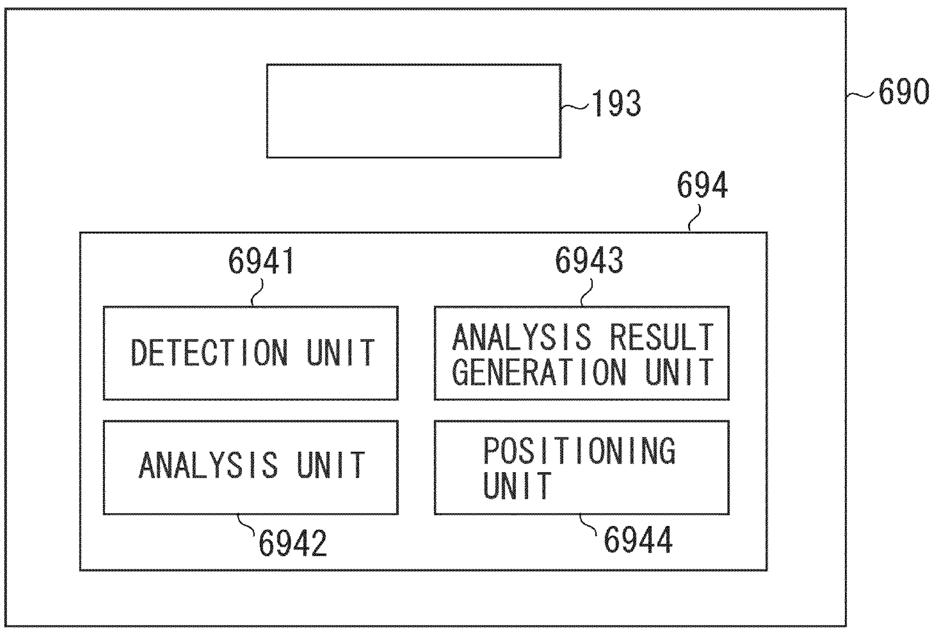

FIG. 6B illustrates an image analysis unit 694 according to the present exemplary embodiment. The image analysis unit 694 includes a detection unit 6941, an analysis unit 6942, an analysis result generation unit 6943, and a positioning unit 6944.

<Image Analysis>

The image analysis unit 694 analyzes the shape of the lamina cribrosa as optic disc periphery shape analysis, and analyzes the curvature of the macula as macula shape analysis.

The detection unit 6941 detects the retina layer, as described in the first exemplary embodiment, and further detects the lamina cribrosa at the optic disc. The positioning unit 6944 performs positioning of tomographic images to generate a three-dimensional shape. To position tomographic images, for example, an evaluation function indicating the similarity of two tomographic images is predefined, and the positioning unit 6944 transforms the tomographic images so that the value of the evaluation function is optimized. The evaluation by the evaluation function may be based on the pixel values (for example, based on a correlation coefficient). Processing for image transformation includes translational movement and rotation by using affine transformation.

Figure 7A:
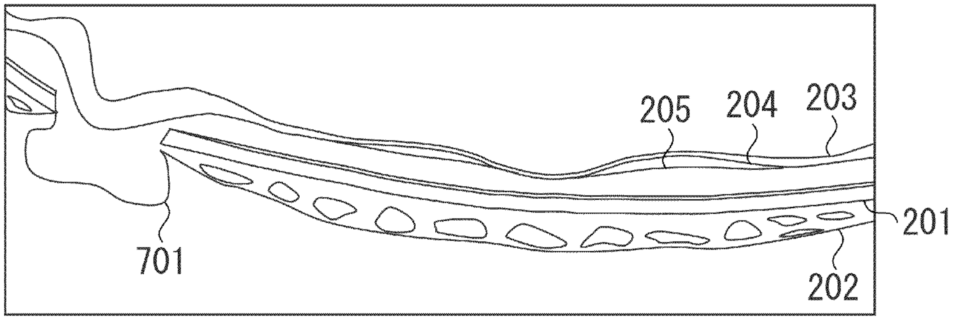
FIGS. 7A and 7B illustrate a tomographic image and a relevant analysis portion, respectively, according to the second exemplary embodiment of the present invention.

FIG. 7A illustrates the shape of the front face of a lamina cribrosa 701. An example method for analyzing the shape of the lamina cribrosa 701 will be described below with reference to FIG. 7B. As a method for analyzing the shape of the lamina cribrosa 701 by the analysis unit 6942, the use of the bowing angle will be described below. The bowing angle can be obtained by connecting two points of a Bruch membrane opening 702 with a straight line, dividing the straight line into four, drawing perpendicular lines BA1, BA2, and BA3 from the three division points toward the lamina cribrosa 701, and assigning BA1, BA2, and BA3 to formula (1), where BA1, BA2, and BA3 indicate the length (distance) of respective perpendicular lines. The larger (more positive) the value of formula (1), the more convex the lamina cribrosa 701 becomes. The smaller (more negative) the value of formula (1), the more W-shaped the lamina cribrosa 701 becomes. In other words, the bowing angle serves as an index for grasping the shape of the lamina cribrosa 701 based on its sign and value.

$$BowingAngle = BA2 - \frac{BA1 + BA3}{2} \quad (1)$$

Figure 7B:
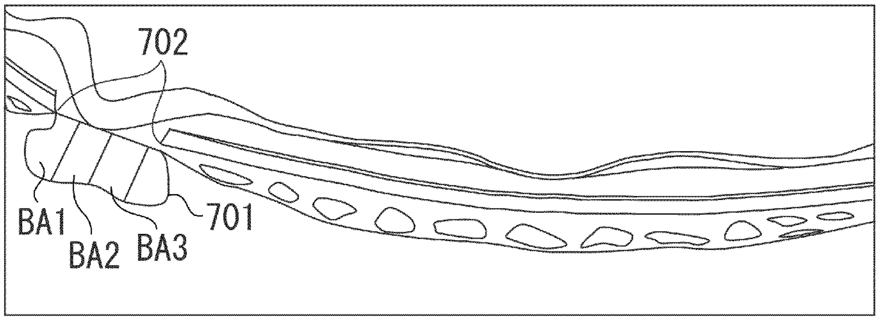

Processing performed by the analysis unit 6942 to analyze the curvature of the macula as macula shape analysis will be described below. Referring to FIGS. 7A and 7B, with the horizontal axis indicating the x-coordinate and the vertical axis indicating the z-coordinate, the analysis unit 6942 calculates the curvature of the boundary line of layers subjected to shape analysis. For example, the boundary 201 between the retinal pigment epithelium and the choroid membrane and the boundary 202 between the choroid membrane and the sclerotic membrane are layers subjected to shape analysis. At each point of the boundary line, a curvature κ can be calculated by formula (2). Whether the shape is convex upward or convex downward is known from the sign of the curvature κ, and the degree of bending in shape is known from the magnitude of the numerical value. Therefore, when the positive sign indicates an upward convex and the negative sign indicates a downward convex, the sign of the curvature κ changing to negative, positive, and then negative in each tomographic image indicates that the shape is in a W shape.

$$\kappa = \frac{\frac{d^2 z}{dx^2}}{\left(1 + \left(\frac{dz}{dx}\right)\right)^{\frac{3}{2}}} \quad (2)$$

Although, in this example, the curvature is calculated based on the boundary line of the tomographic image, the curvature calculation is not limited thereto. A three-dimensional curvature may be calculated based on three-dimensional data.

The analysis result generation unit 6943 generates a shape analysis map and a shape analysis graph of the optic disc and the macula analyzed by the analysis unit 6942.

<Output>

When the signal processing unit 690 completes generation and analysis of each image, the control unit 191 generates output information based on a result of the analysis and outputs the output information to the display unit 192 to display the information.

[Display Screen]

Figure 8:
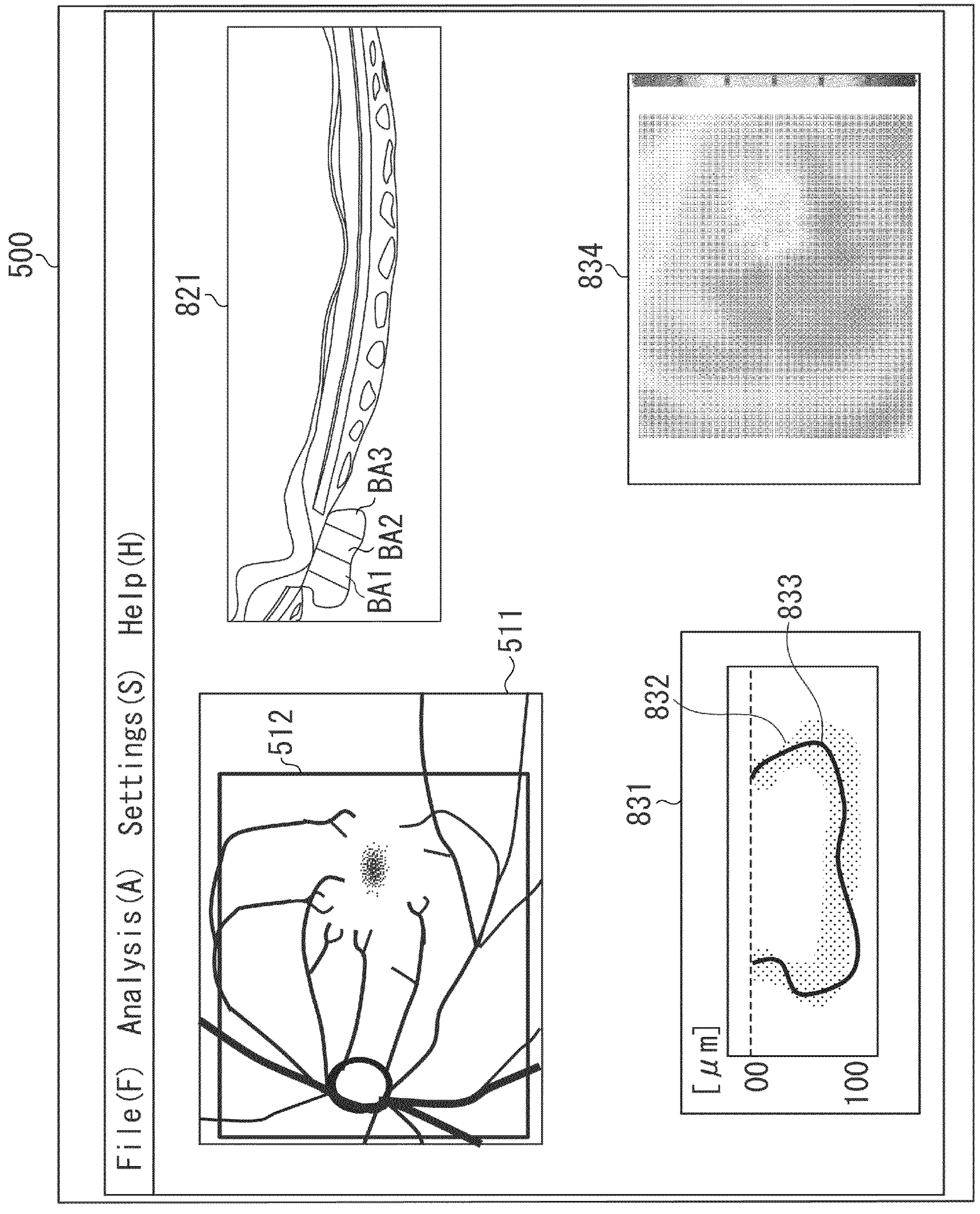
FIG. 8 illustrates an example display of an analysis result according to the second exemplary embodiment.

FIG. 8 illustrates example display of a result of the analysis by the display unit 192 according to the present exemplary embodiment. FIG. 8 illustrates the fundus image 511, a tomographic image 821, analysis results 831 and 834, and the analysis position 512.

Referring to FIG. 8, the analysis result 834 is a macula shape analysis map, and the analysis result 831 is a lamina cribrosa shape graph. Referring to the analysis result 831, a solid line 833 indicates a measured shape of the lamina cribrosa, and a region 832 indicates an example range of a normal lamina cribrosa shape based on a statistical database.

As described above, the present exemplary embodiment enables efficiently presenting a result of analyzing the shape of the optic disc periphery and a result of analyzing the shape of the macula periphery in a tomographic image having a wide viewing angle and a large depth in the depth direction obtained by the SS-OCT. Therefore, in a nearsightedness diagnosis, information for grasping changes in shape of the optic disc and the macula can be efficiently presented.

The above-described first and second exemplary embodiments present a result of measuring the thickness and shape of the optic disc periphery and a result of measuring the thickness and shape of the macula periphery in a tomographic image having a wide viewing angle obtained by the SS-OCT. A third exemplary embodiment of the present invention efficiently presents a result of analyzing a tomographic image having a wide viewing angle obtained by a swept source-polarization sensitive-OCT (SS-PS-OCT).

Figure 9:
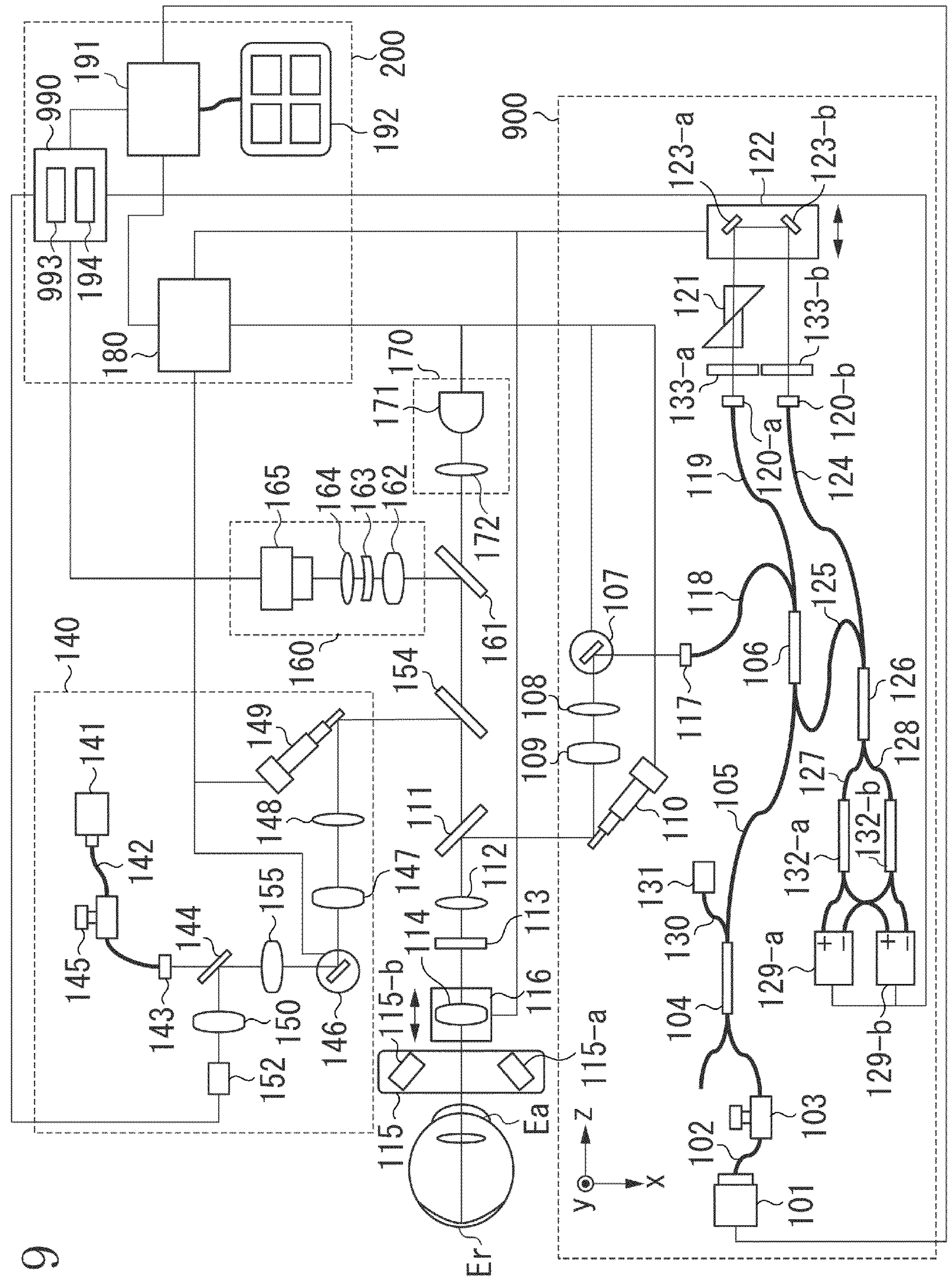
FIG. 9 is a schematic view illustrating an overall configuration of an image processing apparatus according to a third exemplary embodiment of the present invention.

FIG. 9 is a schematic view illustrating an overall configuration of an image processing apparatus according to the present exemplary embodiment. The image processing apparatus according to the present exemplary embodiment includes an SS-PS-OCT 900, the SLO 140, the anterior ocular segment imaging unit 160, the internal fixation lamp 170, and the control unit 200.

The configuration and image generation by the SS-PS-OCT 900 according to the present exemplary embodiment will be described below.

<Configuration of the SS-PS-OCT 900>

The configuration of the SS-PS-OCT 900 will be described below. The configuration of the SS-PS-OCT 900 according to the present exemplary embodiment differs from that according to the first exemplary embodiment in the configuration after λ/4 polarizing plates 113, 133-*a*, and 133-*b* and the fiber coupler 126.

The measuring beam reflected by the dichroic mirror 111 passes through the lens 112 and, then, through the λ/4 polarizing plate 113 with a polarization split surface obliquely installed by 45 degrees with respect to p-polarized light in the s-polarization direction. The λ/4 polarizing plate 113 causes a 90-degree phase shift and applies polarization control to the measuring beam to convert it into circularly polarized light.

The measuring beam having undergone polarization control to be circularly polarized light passes through the focus lens 114 mounted on the stage 116 and the anterior ocular segment Ea of the subject's eye, and then is focused on the retina layer of the fundus Er. The measuring beam radiated onto the fundus Er reflects off and scatters on each retina layer, advances through the above-described optical path (passes through the fiber coupler 106 and the fiber 125), and then reaches the fiber coupler 126.

On the other hand, the reference beam branched by the fiber coupler 106 advances through the fiber 119 and reaches the collimator 120-*a*. The collimator 120-*a* emits the reference beam as parallel light. Similar to the measuring beam, the emitted reference beam passes the λ/4 polarizing plate 133-*a* which is obliquely installed by 22.5 degrees with respect to the p-polarized light in the s-polarization direction. The λ/4 polarizing plate 133-*a* applies polarization control to the reference beam. The reference beam passes through a dispersion compensation glass 121, reflects off the mirrors 123-*a* and 123-*b* on the coherence gate stage 122, passes through the λ/4 polarizing plate 133-*b*, and then returns to the fiber coupler 126. Since the reference beam passes through the λ/4 polarizing plates 133-*a* and 133-*b*, the reference beam returns to the fiber coupler 126 as linearly polarized light.

The measuring beam and the reference beam having reached the fiber coupler 126 are combined into interference light. Then, the interference light advances through the fibers 127 and 128, enters fiber couplers 132-*a* and 132-*b* including a polarization beam splitter, and then is split into two polarized lights having different polarization directions (s-polarized light and p-polarized light in the present exemplary embodiment) with a branching ratio of 50:50. Balanced receivers (photodetectors) 129-*a* and 129-*b* convert respective split lights (interference signals) into electrical signals. Then, a signal processing unit 990 analyzes the converted electrical signals.

[Image Processing]

Processing for image generation by an image generation unit 993 in the signal processing unit 990 will be described below.

<Tomographic Image Generation>

First of all, the image generation unit 993 eliminates fixed pattern noise from the interference signal. The image generation unit averages a plurality of detected A-scan signals to extract fixed pattern noise, and subtracts the fixed pattern noise from the input interference signal, thus eliminating fixed pattern noise.

Then, the image generation unit 993 converts the interference signal into the number of waves based on the wavelength and then performs Fourier transform to generate a tomographic signal.

Applying the above-described processing to the two interference signals having different polarization components generates two tomographic images.

<Luminance Image Generation>

The image generation unit 993 generates a luminance image based on the above-described two tomographic signals.

The generated luminance image is basically the same as the tomographic image generated by the conventional OCT. A pixel value r is calculated by formula (3) where $A_H$ and $A_V$ each indicate a tomographic signal.

$$r=\sqrt{A_H^2+A_V^2} \quad (3)$$

<Retardation Image Generation>

The image generation unit 993 generates a retardation image based on a tomographic image having polarization components perpendicularly intersecting with each other.

Each pixel value δ of the retardation image numerically represents a phase difference between vertical and horizontal polarization components at a position of each pixel constituting the tomographic image. The value δ is calculated by formula (4) where $A_H$ and $A_V$ each indicate the tomographic signal.

$$\delta = \arctan\left[\frac{A_V}{A_H}\right] \quad (4)$$

<Retardation Map Generation>

The image generation unit 993 generates a retardation map based on the retardation image obtained for a plurality of B-scan images.

First of all, the image generation unit 993 detects the retinal pigment epithelium (RPE) in each B-scan image. Since the RPE has the characteristics of canceling polarization, the image generation unit 993 investigates, in each A-scan, the distribution of retardation in a range in the depth direction not including the RPE in the internal limiting membrane (ILM), and then sets the relevant maximum value as a typical value of retardation in the relevant A-scan.

The image generation unit 993 applies the above-described processing to all of the retardation images to generate a retardation map.

<Birefringence Map Generation>

In each A-scan of the generated retardation images, the image generation unit 993 applies linear approximation to the retardation value δ in a range from the ILM to the retinal nerve fiber layer (RNFL), and determines a resultant inclination as the birefringence at the position of the relevant A-scan on the retina. The image generation unit 993 applies this processing to all of the retardation images to generate a birefringence map.

<DOPU Image Generation>

By using formula (5), the image generation unit 993 calculates the Stokes vector S for each pixel based on the obtained tomographic signals $A_H$ and $A_V$ and a phase difference ΔΦ between the two signals.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad (5)$$

However, the image generation unit 993 calculates the phase difference $\Delta\Phi(=\Phi_V-\Phi_H)$ where $\Phi_H$ and $\Phi_V$ indicate phases of the tomographic signals $A_H$ and $A_V$, respectively, obtained when calculating the two tomographic images.

Then, the image generation unit 993 sets a window having a size of about 70 μm in the main scanning direction of the measuring beam and a size of about 18 μm in the depth direction, averages each element of the Stokes vector S calculated for each pixel in each window based on formula (5), and then calculates the degree of polarization uniformity (DOPU) in the relevant window by using formula (6).

$$DOPU=\sqrt{Q_m^2+U_m^2+V_m^2} \quad (6)$$

Qm, Um, and Vm respectively indicate average values of elements Q, U, and V of the Stokes vector S in each window. Applying this processing to all of the windows in the B-scan image enables generating a DOPU image.

The DOPU numerically represents the degree of polarization uniformity. The DOPU value is close to 1 at a portion where polarization is maintained, and smaller than 1 at a portion where polarization is canceled (not maintained). The structure inside the retina has the characteristics that the polarization state is canceled by the RPE. In the DOPU image, therefore, the DOPU value at a portion corresponding to the RPE is smaller than that in other regions. Since the DOPU image represents layers in which polarization of the RPE is canceled, the RPE can be imaged even in a case where the RPE is deformed or lost because of illness.

<DOPU Map Generation>

The image generation unit 993 investigates the DOPU value in the depth direction in each A-scan of the previously generated DOPU image. Then, the image generation unit 993 sets the average value (or the maximum or minimum value) of the DOPU value within a threshold value range (for example, 0.4 to 0.8) as the DOPU value for the relevant A-scan. The image generation unit 993 applies this processing to all of the obtained DOPU images to generate a DOPU map.

<Output>

When the signal processing unit 990 completes generation and analysis of each image, the control unit 191 generates output information based on a result of the image generation and analysis and outputs the output information to the display unit 192 to display the information.

<Display Screen>

Figure 10:
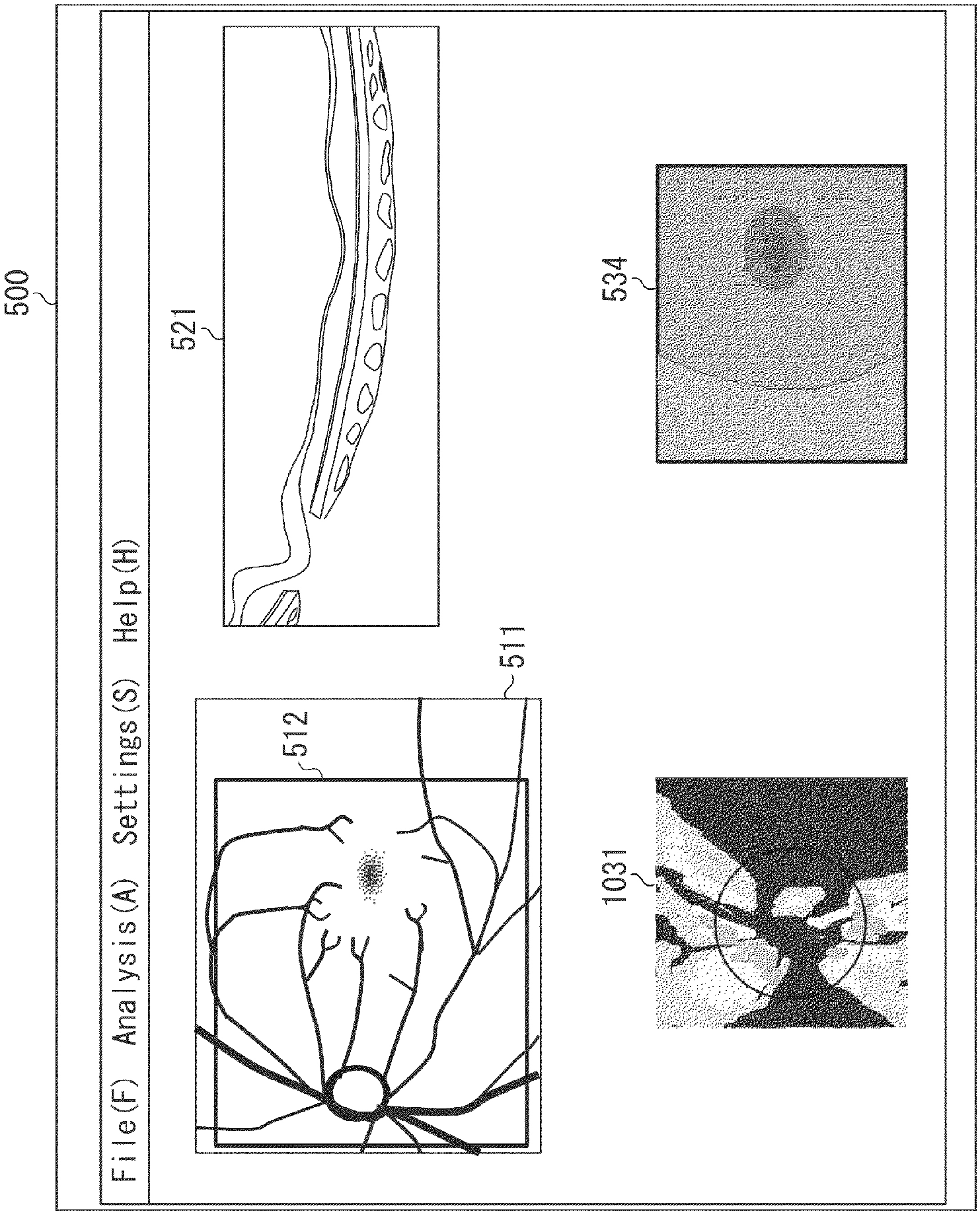
FIG. 10 illustrates an example display of an analysis result according to the third exemplary embodiment.

FIG. 10 illustrates example display of a result of the analysis by the display unit 192 according to the present exemplary embodiment. FIG. 10 illustrates the fundus image 511, the tomographic image 521, and analysis results 1031 and 534.

Referring to FIG. 10, the analysis result 1031 indicates a birefringence map of the optic disc periphery. The birefringence map of the analysis result 1031 directly maps the birefringence value. Therefore, even when the thickness of the RNFL remains unchanged, a change in the fiber structure can be drawn as a change in birefringence. The analysis result 534 is a layer thickness map. The layer thickness map displays, for example, the thickness of the RNFL and GCL or the thickness of the choroid membrane.

As described above, the present exemplary embodiment enables efficiently presenting a result of analyzing the function of the optic disc periphery and a result of analyzing the thickness of the macula periphery in a tomographic image having a wide viewing angle and a large depth in the depth direction obtained by the SS-PS-OCT. Thus, a loss of the RNFL at the optic disc, a loss of the GCL at the macula, and a reduction in thickness of the choroid membrane can be grasped at the same time. Therefore, in a glaucoma diagnosis, information for grasping changes in layer thickness at the optic disc and the macula can be efficiently presented.

The above-described first to third exemplary embodiments present a result of measuring the optic disc periphery and a result of measuring the macula periphery in a tomographic image having a wide viewing angle obtained by the SS-OCT. In a fourth exemplary embodiment of the present invention, a correlation between these results is analyzed and a result of the analysis are presented.

[Image Processing]

<Image Analysis>

The image analysis unit 694 performs the processing illustrated in the first to third exemplary embodiments to analyze the optic disc and the macula. The analysis result generation unit 6943 generates a result of comparing analysis parameters for the optic disc and analysis parameters for the macula with the statistical database.

[Display Screen]

Figure 11:
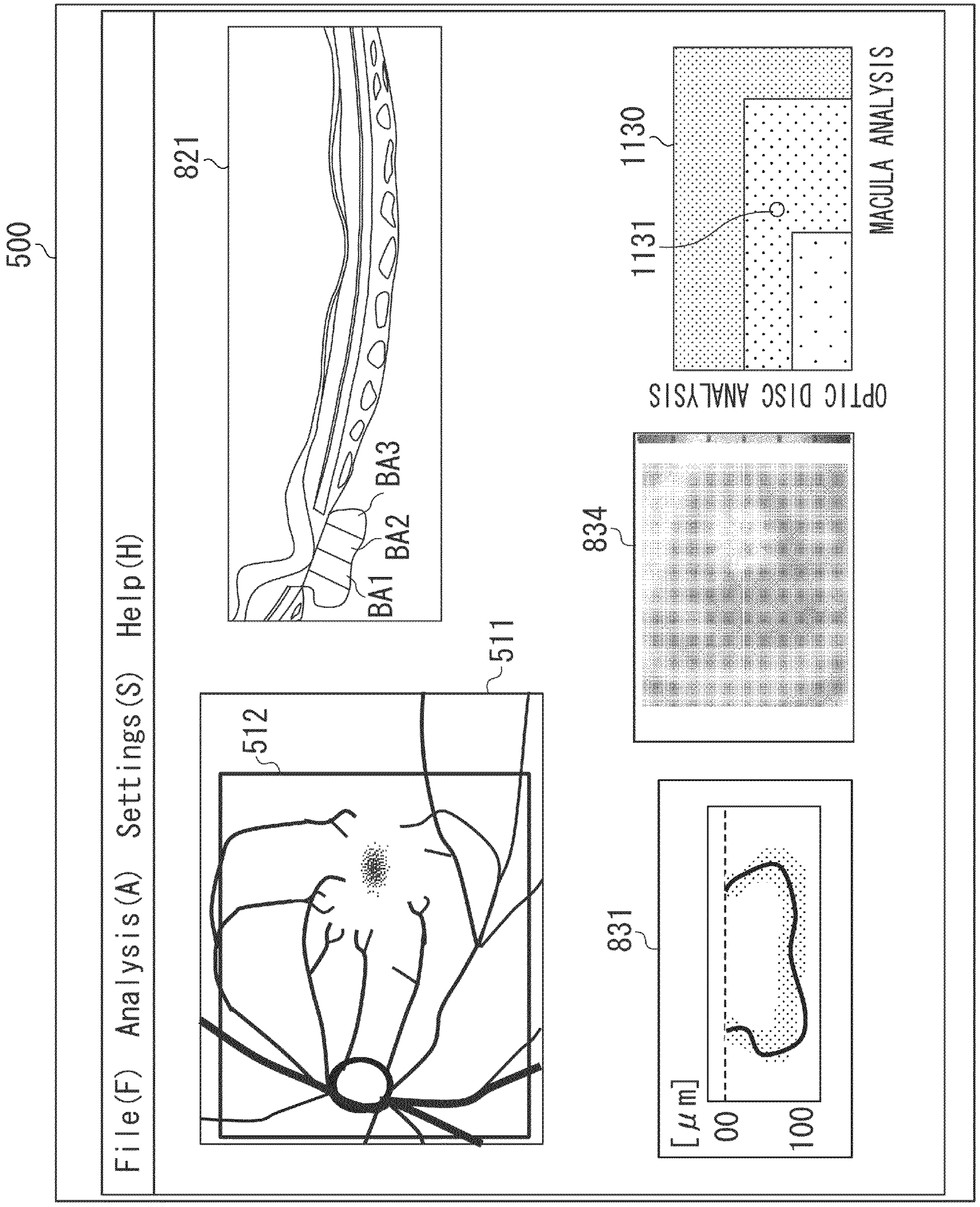
FIG. 11 illustrates an example display of an analysis result according to a fourth exemplary embodiment of the present invention.

FIG. 11 illustrates example display of a result of the analysis by the display unit 192 according to the present exemplary embodiment. Referring to FIG. 11, an analysis result 1130 displays, as a map, the statistics database of analysis parameters for the optic disc and analysis parameters for the macula. A plot 1131 indicates the analysis result plotted on the statistics database. Referring to the analysis result 1130, the vertical axis indicates the result of the optic disc analysis and the horizontal axis indicates the result of the macula analysis. For example, values obtained by analyzing the lamina cribrosa of the optic disc and values obtained by analyzing the shape of the macula are compared with the statistics database. Referring to the statistical database map of the analysis result 1130, the central shaded portion indicates a normal value range, and the darker and lighter shaded portions each indicate abnormal value ranges.

Forms of analysis results are not limited thereto. A correlation between a thickness and a shape, and a correlation between thicknesses may be presented as an analysis result.

As described above, the present exemplary embodiment enables efficiently presenting a correlation between a result of analyzing the function of the optic disc periphery and a result of analyzing the thickness of the macula periphery in a tomographic image having a wide viewing angle and a large depth in the depth direction obtained by the SS-OCT. Thus, a plurality of analysis parameters for the optic disc and the macula can be presented with respective correlations arranged.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-082375 filed Mar. 30, 2012, which is hereby incorporated by reference herein in its entirety.

What is claimed is:

1. An image processing apparatus comprising:

an obtaining unit configured to obtain a tomographic image including an optic disc portion and a macula portion of a fundus of a subject's eye;

an analysis unit configured to analyze the optic disc portion and the macula portion of the fundus in the tomographic image, analyzing the optic disc portion including calculating a bowing angle of a lamina cribrosa, analyzing the macula portion including calculating a curvature of a layer boundary in the fundus; and a display control unit configured to display side-by-side, on a display unit, information based on the bowing angle of the lamina cribrosa and the curvature of the layer boundary in the fundus.

2. An image processing apparatus comprising:

an obtaining unit configured to obtain a tomographic image including an optic disc portion and a macula portion of a fundus of a subject's eye;

an analysis unit configured to analyze the optic disc portion and the macula portion of the fundus in the tomographic image, analyzing the optic disc portion including calculating a bowing angle of the lamina cribrosa, analyzing the macula portion including calculating a curvature of a boundary between retina layers; and a display control unit configured to display, on a display unit, information based on the bowing angle of the lamina cribrosa and the curvature of a boundary line between retina layers.

3. An image processing apparatus comprising:

an obtaining unit configured to obtain a tomographic image including an optic disc portion and a macula portion of a fundus of a subject's eye; and an analysis unit configured to analyze the optic disc portion and the macula portion of the fundus in the tomographic image, analyzing the optic disc portion including calculating a bowing angle of the lamina cribrosa, analyzing the macula portion including calculating a curvature of a boundary between retina layers.

* * * * *